US006524390B1

(12) United States Patent
Jones

(10) Patent No.: US 6,524,390 B1
(45) Date of Patent: *Feb. 25, 2003

(54) HANDWASHING TECHNIQUE ANALYSIS

(76) Inventor: C. Kerry Jones, 1347 Leeper, South Bend, IN (US) 46617

( * ) Notice: Subject to any disclaimer, the term of this patent is extended or adjusted under 35 U.S.C. 154(b) by 0 days.

This patent is subject to a terminal disclaimer.

(21) Appl. No.: 08/441,823

(22) Filed: May 16, 1995

(51) Int. Cl.[7] .................................................. B08B 7/02
(52) U.S. Cl. ......................................................... 134/1
(58) Field of Search ........................ 252/408.1, 301.16; 134/1, 26, 42, 29; 128/633

(56) References Cited

U.S. PATENT DOCUMENTS

| 3,640,889 A | | 2/1972 | Stewart ............... 252/301.2 R |
| 4,554,098 A | * | 11/1985 | Klisch et al. |
| 4,610,806 A | * | 9/1986 | Rosen .................... 252/301.16 |
| 4,938,224 A | * | 7/1990 | Rysavy ........................ 128/633 |
| 4,965,063 A | | 10/1990 | Casey et al. .................. 424/7.1 |
| 4,992,256 A | | 2/1991 | Skaggs et al. ............... 424/7.1 |
| 5,037,485 A | * | 8/1991 | Chromecek et al. ........... 134/7 |
| 5,098,691 A | | 3/1992 | Simone et al. ............... 424/7.1 |
| 5,304,253 A | * | 4/1994 | Grant .......................... 134/26 |
| 5,334,258 A | * | 8/1994 | Osano et al. ................. 134/42 |
| 5,403,403 A | * | 4/1995 | Lee .............................. 134/42 |
| 5,900,067 A | * | 5/1999 | Jones ............................. 134/1 |

FOREIGN PATENT DOCUMENTS

WO        94-347398/43    *   3/1993

OTHER PUBLICATIONS

Brochure of Glo Germ Company, "Glo Germ" can help you become a "Germ Detective"!, 1968.*

Christopher Phillips, "Handy Hygiene", Sep. 13, 1989, Nursing Times, vol. 85, No. 37.

William M. Marcil, "Handwashing Practices Among Occupational Therapy Personnel", Jun. 1993, The American Journal of Occupational Therapy, vol. 47, No. 6.

Bradley N. Doebbeling, M.D., et al., "Comparative Efficacy of Alternative Hand–Washing Agents in Reducing Nosocomial Infections in Intensive Care Units", Jul. 9, 1992, The New England Journal of Medicine.

Elaine Larson, "Hand Washing—It's Essential—Even If You Use Gloves", Jul. 1989, Journal of Nursing.

Brochure entitled "Glo Germ Can Help You Become a Germ Detective"! (date unknown).

* cited by examiner

Primary Examiner—Jill Warden
(74) Attorney, Agent, or Firm—Emrich & Dithmar

(57) ABSTRACT

A handwashing medium which may be in liquid, cream, powder or spray form is provided with a detection agent such as an invisible fluorescent additive, which combination is then rubbed onto one's hands using the individual's handwashing technique and is allowed to dry. The individual's hands are rinsed with water as in the normal handwashing fashion and the hands are then exposed to an activating agent such as an ultraviolet (UV) light source. Areas missed during handwashing retain the fluorescent additive and are clearly visible due to fluorescence. The method is useful in evaluating one's handwashing technique and has applicability anywhere cleanliness is required such as in hospitals, clinics, restaurants, etc., and may be used as an instructional aid in teaching young children proper hygiene techniques. The invisible fluorescent additive in a handwashing medium may also be used in determining patterns of body part contact such as contact with one's hands or feet in a given area by applying the invisible fluorescent additive to a body part and exposing the area to UV light to detect the presence of residue of the fluorescent agent.

10 Claims, 3 Drawing Sheets

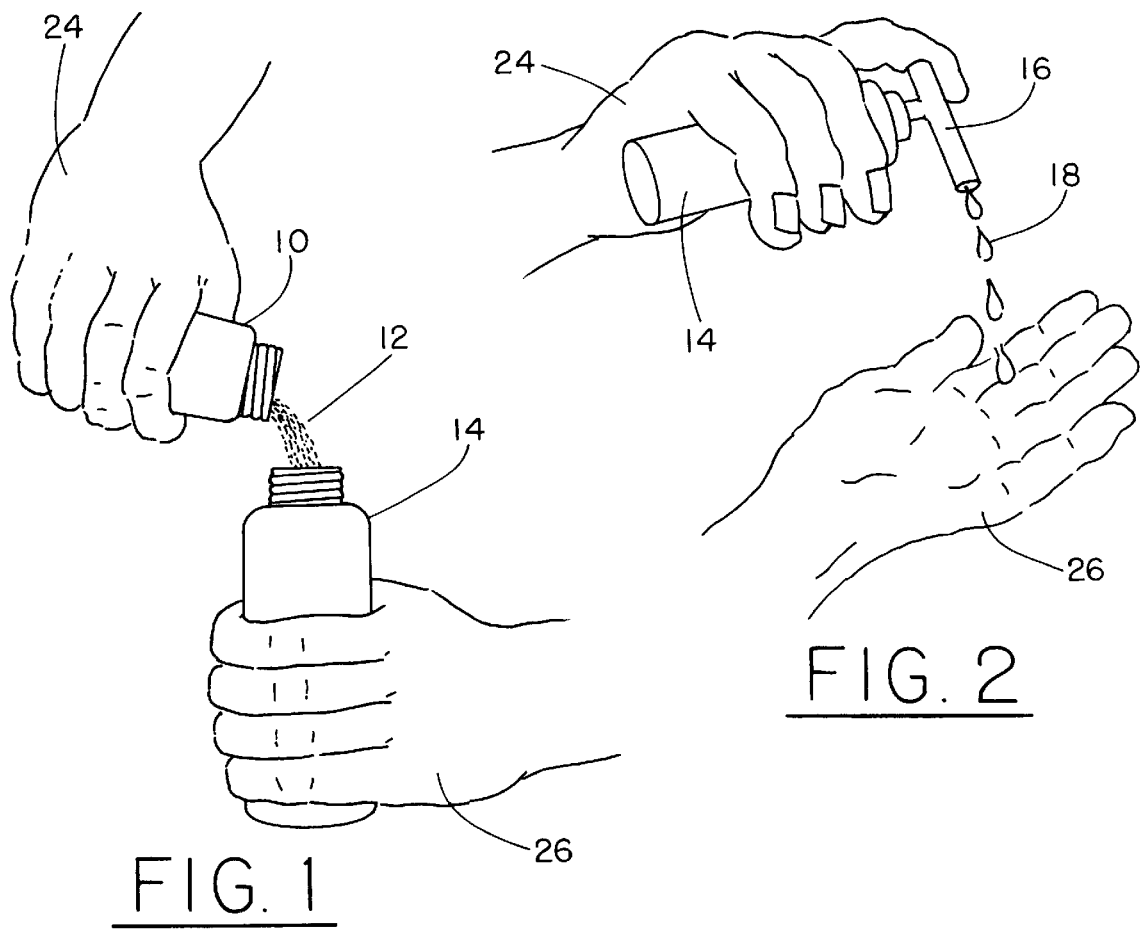
FIG. 1
FIG. 2
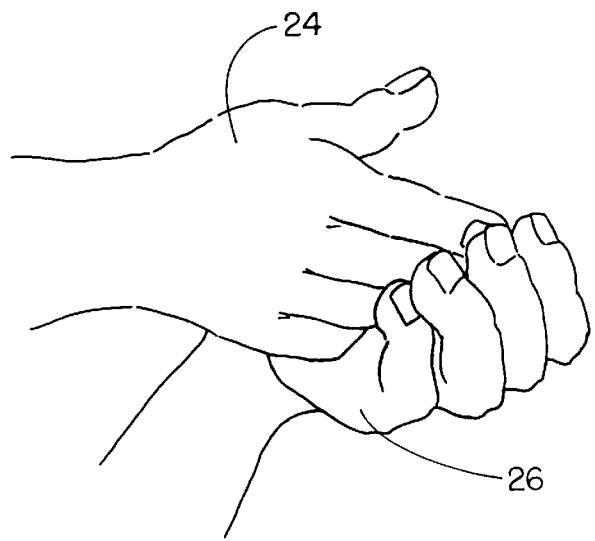
FIG. 3

HANDWASHING TECHNIQUE ANALYSIS

FIELD OF THE INVENTION

This invention relates generally to personal hygiene and is particularly directed to a method for evaluating the effectiveness of one's handwashing technique.

BACKGROUND OF THE INVENTION

Cleanliness is essential for good health. The spread of infectious disease has reached epidemic proportions in many parts of the world. Even in the more technically advanced countries, the increase in the spread of contagious diseases, which in many cases is fatal to the victim, has reached an alarming level and has caused great fear and anxiety. Because of the nature of human beings and the manner in which they interrelate, contagious disease and illness is frequently transmitted by hand. It has been determined that some organisms live for 150 minutes on the skin. Because many patients can be handled in a 2½ hour period, the risk of cross-infection is clearly great. The need for a high degree of cleanliness in certain environments such as hospitals, clinics, restaurants etc., is thus obvious. Great precautions are taken in these types of facilities to minimize the transfer of disease-causing microbes among people. In many cases, the transfer of disease is caused by improper cleaning such as of one's hands or by the improper or unauthorized handling of contaminated materials. Frequently, access to and the handling of contaminated materials or objects is inadvertent and the individual involved may not be aware that he or she has touched or been exposed to the source of contamination.

This invention addresses the aforementioned problems encountered in the prior art by providing a method which permits an individual to evaluate the effectiveness of his or her handwashing technique as well as to apprise the individual of his or her patterns of hand contact in a given area.

OBJECTS AND SUMMARY OF THE INVENTION

Accordingly, it is an object of the present invention to provide a method for evaluating the effectiveness of one's handwashing technique.

It is another object of the present invention to determine the extent of cleanliness of a body part after it has been washed.

Yet another object of the present invention is to instruct people, such as young children, in the area of personal hygiene and thus reduce the spread of infectious disease.

A further object of the present invention is to provide a simple, foolproof method for detecting contamination of a body part or object such as by accidental touching.

A still further object of the present invention is to provide information regarding one's hand contact pattern within a given area.

Another object of the present invention is to provide a handwashing medium which also permits the user to determine the effectiveness of his or her handwashing technique.

The present contemplates a method for evaluating a person's handwashing technique comprising the steps of: applying a handwashing medium containing a detection agent to the person's hands; moving the person's hands into contact with one another in accordance the handwashing technique of the person so as to spread the handwashing medium over both hands of the person; rinsing both hands in water so as to remove the handwashing medium from the hands; and directing an activating agent onto the person's hands for rendering the detection agent visible and determining the presence of any of the detection agent on the hands indicating an unwashed portion of the hands.

BRIEF DESCRIPTION OF THE DRAWINGS

The appended claims set forth those novel features which characterize the invention. However, the invention itself, as well as further objects and advantages thereof, will best be understood by reference to the following detailed description of a preferred embodiment taken in conjunction with the accompanying drawings, where like reference characters identify like elements throughout the various figures, in which:

FIG. 1 is a simplified illustration of adding a detection agent such as fluorescent powder to a container of handwashing lotion in accordance with one aspect of the present invention;

FIG. 2 is a simplified illustration of the dispensing of a handwashing lotion on one's hands in accordance with another aspect of the present invention;

FIG. 3 is a simplified illustration of the manner in which the handwashing lotion containing the fluorescent powder is spread over one's hands in accordance with a typical handwashing technique;

DETAILED DESCRIPTION OF THE PREFERRED EMBODIMENTS

Figure 4:
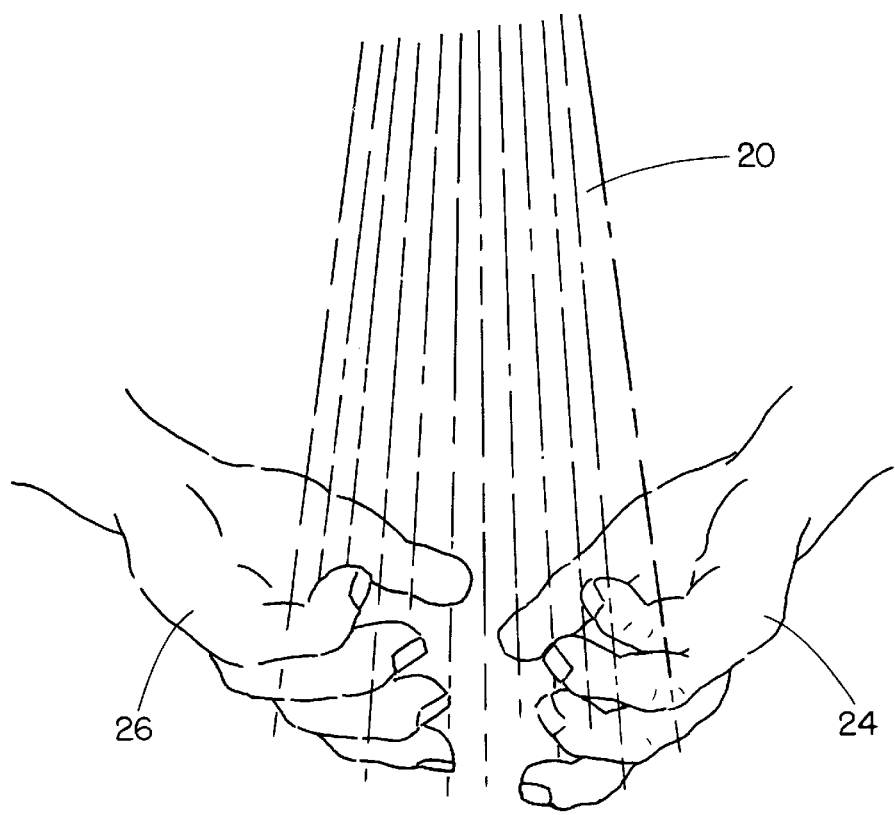
FIG. 4 is a simplified illustration of rinsing the handwashing lotion from the hands using a stream of water in accordance with another aspect of the present invention.

Referring to FIGS. 1–5, there is shown in simplified schematic diagram form the steps involved in carrying out the handwashing technique analysis of the present invention. The various figures illustrate a pair of hands on which the inventive handwashing technique analysis is applied, where the right and left hands are respectively identified by element numbers 24 and 26.

In FIG. 1, a fluorescent powder 12 is shown being dispensed from a first container 10 into a second container 14 containing a handwashing medium. The fluorescent agent may be in the form of a powder, as illustrated, a liquid, a cream or a spray. It is essential that the fluorescent powder 12 be inconspicuous, or perhaps even invisible, so that when one applies the fluorescent powder and a handwashing medium as described below to one's hands in a washing motion, the fluorescent agent is essentially not visible during this handwashing process. While this embodiment of the invention contemplates the use of a fluorescent agent, virtually any essentially invisible detection agent responsive to an activating agent may be used in carrying out the present invention.

Referring to FIG. 2, the next step in the process is shown as applying the handwashing solution 18 from the second container 14 using a dispensing mechanism 16 onto one of the hands of the user. The handwashing medium 18 may also be in the form of a liquid, as illustrated, a cream, a powder or a spray, with any of the more conventional handwashing media adapted for use with the present invention. As shown in FIG. 2, the handwashing solution 18 is in the form of a series of drops deposited upon the user's left hand 26. FIG. 3 shows the user's right and left hands 24, 26 in engaging contact in a handwashing motion for distributing the handwashing solution containing the fluorescent agent over both hands. After the fluorescent agent and the handwashing solution combination is rubbed over both hands as shown in FIG. 3, the hands are allowed to dry.

Figure 5:
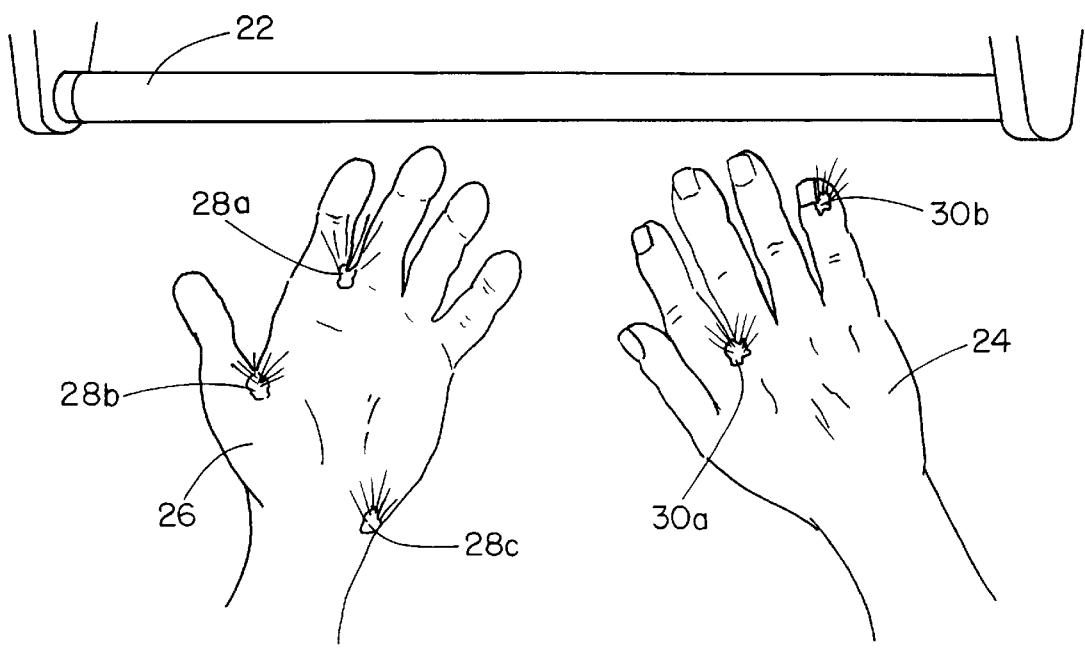
FIG. 5 is a simplified illustration of a pair of hands on which there remains a residue of fluorescent powder following washing of the hands, with an activating agent such as an ultraviolet light source directed onto the hands so as to render the fluorescent powder visible in accordance with another aspect of the present invention.

The handwashing solution is then rinsed from the hands. by means of a stream of water 20 as shown in FIG. 4. The water rinses the handwashing solution from the hands, leaving a residue of the fluorescent agent on those portions of the hands which have not been exposed to and cleaned by the handwashing solution. By irradiating hands 24 and 26 with an ultraviolet (UV) light source 22, the fluorescent residue is activated and readily visible in the form of fluorescent agent residue deposits 28a, 28b, and 28c on the left hand 26 and fluorescent agent residue deposits 30a and 30b on the right hand 24 as shown in FIG. 5. Areas where the fluorescent agent remains on the hands after rinsing of the handwashing solution indicates to the user those portions of the hands which have not been cleaned by the handwashing solution. In this manner, the user can alter his or her handwashing technique to expose all surface portions of the hands to the handwashing solution for more effectively cleaning the hands. While this embodiment of the invention contemplates a UV light source used with a fluorescent powder, virtually any combination of an invisible detection agent and a complementary activating agent may be used in carrying out the present invention.

Figure 6:
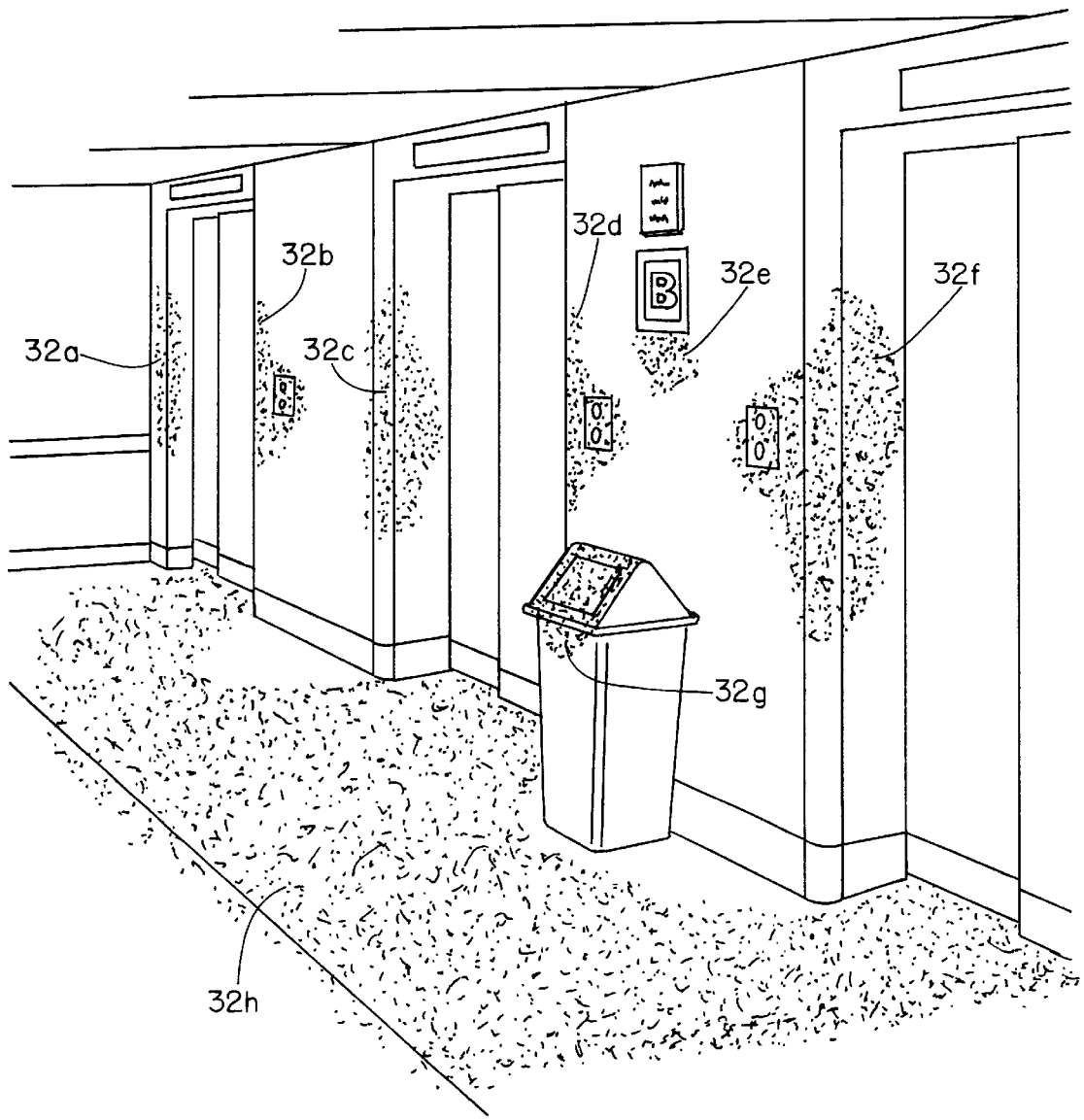
FIG. 6 is an illustration of a room on various portions of which there has been deposited a detection agent such as fluorescent powder by contact by persons within the room in accordance with another aspect of the present invention.

Referring to FIG. 6, there is shown a space in which various areas have been marked by cross-hatching and are identified by element numbers 32a–32h. In accordance with another aspect of the invention, the invisible fluorescent agent, or another detection agent, may be applied to one's body parts and during the course of carrying out one's activities in a given area, the body part come in contact with areas 32a–32h within the space resulting in deposit of the fluorescent agent on various surfaces within the space. Ultraviolet light, or other complementary activating agent, is then used to irradiate the space, activating the fluorescent agent deposited on various surfaces to indicate those surfaces upon which hand or foot contact has occurred. In this manner, those surfaces which are subject to frequent body part contact such as contact with the hands or feet of one or more individuals are indicated as areas for frequent and more intensive cleaning for improved hygiene and sanitation.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

I claim:

1. A method for evaluating a person's handwashing technique comprising the steps of:
   adding an invisible detection agent to a handwashing medium;
   applying a handwashing medium containing the invisible detection agent to the person's hands;
   moving the person's hands into contact with one another in accordance with the handwashing technique of the person so as to spread said handwashing medium over both hands of the person;
   rinsing both hands in water so as to remove said handwashing medium from the hands and said detection agent from portions of the hands exposed to and cleaned by said handwashing medium; and
   directing an activating agent onto the person's hands for rendering said detection agent visible and determining the presence of any of said detection agent on the hands indicating an unwashed portion of the hands.

2. The method of claim 1 wherein said handwashing medium is in liquid, cream, powder or spray form.

3. The method of claim 2 wherein said detection agent is in liquid, cream, powder or spray form.

4. The method of claim 1 wherein said detection agent is a fluorescent material.

5. The method of claim 4 wherein said activating agent is an ultraviolet light source.

6. An arrangement for washing one's hands and for indicating those portions of the hands which are not cleaned during the handwashing process, said arrangement comprising:
   a washing agent for cleaning the hands when applied to the hands;
   a detection agent disposed in said washing agent and generally invisible to the eye;
   water for rinsing the hands and washing away said washing agent wherein said detection agent remains on portions of the hands not exposed to and cleaned by said washing agent after the hands are rinsed with water and said washing agent is washed away:
   an activating agent directed onto the hands for activating said detection agent for indicating those portions of the hands which have not been cleaned during the handwashing process.

7. The arrangement of claim 6 wherein said washing agent is in liquid, cream, powder or spray form.

8. The arrangement of claim 7 wherein said detection agent is in liquid, cream, powder or spray form.

9. The arrangement of claim 6 wherein said detection agent is a fluorescent material.

10. The arrangement of claim 9 wherein said activating agent is an ultraviolet light source.

* * * * *